US006255534B1

(12) United States Patent
Demuth et al.

(10) Patent No.: US 6,255,534 B1
(45) Date of Patent: *Jul. 3, 2001

(54) PREPARATION OF CARBONYL COMPOUNDS

(75) Inventors: Dirk Demuth, Mannheim; Thomas Fetzer, Speyer; Volker Pratsch, Mannheim; Thomas Wendrich, Carlsberg; Helmuth Menig, Friedelsheim; Ludwig Wambach, Schwetzingen; Klaus Harth, Altleiningen, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,851

(22) Filed: Feb. 1, 1999

(30) Foreign Application Priority Data

Mar. 16, 1998 (DE) .............................................. 198 11 288

(51) Int. Cl.[7] .................................................. C07C 45/29
(52) U.S. Cl. ......................... 568/473; 568/471; 568/402; 502/208
(58) Field of Search ................................. 568/471, 473, 568/402, 470, 472; 502/208; 420/502

(56) References Cited

U.S. PATENT DOCUMENTS

| 3,948,997 | 4/1976 | Howe et al. | 260/596 |
| 4,282,374 | 8/1981 | Engelbach et al. | 568/471 |
| 4,555,583 | * 11/1985 | Toyoda et al. | 568/473 |
| 4,814,513 | 3/1989 | Graf et al. | 568/471 |

* cited by examiner

Primary Examiner—Sreeni Padmanabhan

(74) Attorney, Agent, or Firm—Keil & Weinkauf

(57) ABSTRACT

Carbonyl compounds of the formula

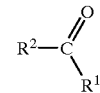

(I)

where $R^1$ is a hydrogen atom or an alkyl radical having from 1 to 3 carbon atoms, $R^2$ is a hydrogen atom, an unsubstituted or $C_1$–$C_3$-alkyl-monosubstituted to -trisubstituted $C_2$–$C_4$-alkenyl radical or a radical of the formula

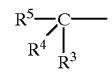

(II)

where $R^3$ is a hydrogen atom or together with $R^4$ is an oxygen atom, $R^4$ is the radical $OR^6$ or together with $R^3$ is an oxygen atom, $R^5$ is a hydrogen atom, an alkyl radical having from 1 to 8 carbon atoms, an unsubstituted or $C_1$–$C_3$-alkyl-monosubstituted to -trisubstituted $C_2$–$C_4$-alkenyl radical or a cyclohexyl or cyclopentyl radical and $R^6$ is an alkyl radical having from 1 to 4 carbon atoms, a cyclohexyl or cyclopentyl radical or a radical of the formula —$CH_2$—CHO or —$CH_2$—$CH_2$—O—$CH_2$—CHO, are prepared by gas-phase oxidation of methanol or alcohols of the formula

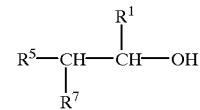

(III)

where $R^1$ and $R^5$ are as defined above, by means of an oxygen-containing gas in the presence of copper- and/or silver-containing catalysts, the catalyst system used comprising at least one phosphorus-containing copper- and/or silver-containing catalyst.

14 Claims, No Drawings

PREPARATION OF CARBONYL COMPOUNDS

The present invention relates to a novel process for preparing carbonyl compounds by gas-phase oxidation of alcohols by means of an oxygen-containing gas in the presence of a catalyst system comprising at least one phosphorus-containing copper- and/or silver-containing catalyst or a catalyst bed comprising an essentially phosphorus-free and at least one phosphorus-containing copper- and/or silver-containing catalyst.

Processes for preparing carbonyl compounds by gas-phase oxidation over copper and/or silver catalysts in the presence of volatile phosphorus compounds are known from the prior art.

Thus, EP-A 007 570 describes a process for preparing glyoxal by gas-phase oxidation of ethylene glycol by means of oxygen over a copper-containing oxidation catalyst in the presence of phosphorus compounds which are volatile under the reaction conditions, in which from 1 to 100 ppm of phosphorus, based on ethylene glycol used, are introduced with the starting compounds. These processes give unsatisfactory glyoxal yields of up to 70 mol %, based on ethylene glycol reacted.

According to the processes of U.S. Pat. No. 4,282,374 and U.S. Pat. No. 4,503,261, the gas-phase oxidation of ethylene glycol over copper catalysts or over a layer catalyst comprising copper and silver crystals gives advantageous results in respect of the life of the catalysts and the glyoxal yield if the reaction is carried out in the presence of a volatile phosphorus compound, where the amount of phosphorus (calculated as P) is from 1 to 100 ppm or from 0.5 to 20 ppm, based on the weight of ethylene glycol, and the phosphorus is introduced with the starting compounds upstream of the catalyst bed. However, when these processes are operated for a prolonged period it has been found that the glyoxal yield and product purity become increasingly poor as the duration of the experiment increases. This disadvantage is attributable to increased formation of formaldehyde and of $CO/CO_2$.

EP-B 0 271 812 proposes, for the preparation of carbonyl compounds such as glyoxal, a gas-phase oxidation of alcohols by means of an oxygen-containing gas in the presence of copper- or silver-containing catalysts and a phosphorus compound which is volatile under the reaction conditions, in which process the phosphorus compound is mixed into the gaseous starting mixture in one portion in an amount of less than 0.5 ppm, based on the weight of alcohol used and calculated as phosphorus, prior to the reaction over the catalyst. According to the process described in EP-B 0 271 812, glyoxal is obtained in yields of up to 80 mol %.

Furthermore, DE-A 19 23 048 discloses a process for preparing carbonyl compounds by gas-phase oxidation of hydroxy compounds over catalyst beds comprising copper-phosphorus catalysts containing from 1 to 5% by weight of phosphorus. This process gives unsatisfactory glyoxal yields.

The abovementioned processes of the prior art have the disadvantage of an unsatisfactory yield. In the known processes, glyoxal is obtained as an aqueous solution contaminated by glycol aldehyde, formaldehyde and organic acids. Further undesirable by-products are the combustion products $CO$, $CO_2$ and $H_2O$. As a consequence of the by-products, the known processes have the additional disadvantages of unsatisfactory catalyst lives.

In addition, the presence of formaldehyde in the glyoxal is highly undesirable for many applications of glyoxal because of the toxicological properties and the high reactivity of formaldehyde. Since formaldehyde can be removed from the crude glyoxal only at considerable expense and with acceptance of yield losses, for instance by treatment with steam or by chemical reaction, an improved process is needed.

It is an object of the present invention to provide a process which allows glyoxal to be prepared by catalytic gas-phase oxidation of ethylene glycol while largely avoiding the formation of undesirable by-products, even for long operating times.

We have found that this object is achieved, in a process for preparing carbonyl compounds of the formula

(I)

where $R^1$ is a hydrogen atom or an alkyl radical having from 1 to 3 carbon atoms, $R^2$ is a hydrogen atom, an unsubstituted or $C_1$–$C_3$-alkyl-monosubstituted to -trisubstituted $C_2$–$C_4$-alkenyl radical or a radical of the formula

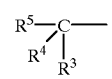

(II)

where $R^3$ is a hydrogen atom or together with $R^4$ is an oxygen atom, $R^4$ is the radical $OR^6$ or together with $R^3$ is an oxygen atom, $R^5$ is a hydrogen atom, an unsubstituted or $C_1$–$C_3$-alkyl-monosubstituted to -trisubstituted $C_2$–$C_4$-alkenyl radical, an alkyl radical having from 1 to 8 carbon atoms or a cyclohexyl or cyclopentyl radical and $R^6$ is an alkyl radical having from 1 to 4 carbon atoms, a cyclohexyl or cyclopentyl radical or a radical of the formula —$CH_2$—CHO or —$CH_2$—$CH_2$—O—$CH_2$—CHO, by gas-phase oxidation of methanol or alcohols of the formula

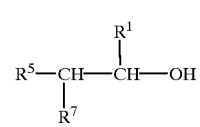

(III)

where $R^1$ and $R^5$ are as defined above and $R^7$ is a hydrogen atom or a radical $OR^8$ and $R^8$ is a hydrogen atom, an alkyl radical having from 1 to 4 carbon atoms, a cyclohexyl or cyclopentyl radical or a radical of the formula —$CH_2$—$CH_2$—OH or —$CH_2$—$CH_2$—O—$CH_2$—$CH_2$—OH, by means of an oxygen-containing gas in the presence of copper- and/or silver-containing catalysts and in the presence or absence of a phosphorus compound which is volatile under the reaction conditions in such an amount that the amount of phosphorus (calculated as P) is up to 20 ppm, based on the total amount of alcohol used, by the improvement which comprises using a catalyst system comprising at least one phosphorus-containing copper- and/or silver-containing catalyst.

In a further embodiment of the process of the present invention, the catalyst system used is a catalyst bed comprising an essentially phophorus-free and at least one phosphorus-containing copper- and/or silver-containing catalyst. In the novel process, glyoxal is obtained from ethylene glycol in long-term-continuous operation in high yield and purity and with a significantly reduced formaldehyde content. The novel process is also technically simple to implement in large-scale plants.

Reduction of the hot spot temperatures also results in an increased operating life of the catalyst in the reactor.

In the alcohols of the formula III, alkyl radicals are, for example, methyl, ethyl, propyl or butyl radicals. In the process of the present invention, terminal hydroxyl groups are converted into aldehyde groups and secondary hydroxyl groups are converted into keto groups.

Examples of starting compounds of the formula III are:
HO—CH$_2$—CH$_2$—OH, H$_3$COCH$_2$—CH$_2$OH, CH$_3$—CH$_2$OH, C$_2$H$_5$OCH$_2$—CH$_2$OH, H$_3$C—CH(OH)—CH$_2$—OH, C$_2$H$_5$—CH(OH)—CH$_2$OH,

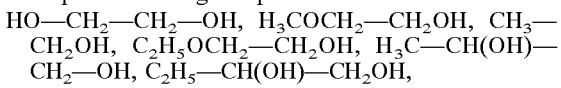

HO—(CH$_2$)$_2$—O—(CH$_2$)$_2$—OH,

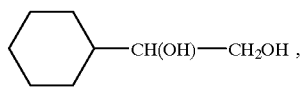

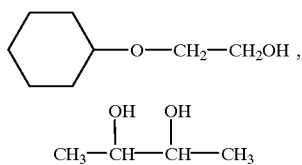

The gas-phase oxidation of the alcohol by means of the oxygen-containing gas over the copper- and/or silver-containing catalysts is carried out in a manner known per se, e.g. at from 225 to 500° C.

Examples of suitable copper- and/or silver-containing catalysts are metallic copper or silver, copper-containing or silver-containing alloys or compounds with metals or nonmetals which may further comprise phosphorus or, in the case of the phosphorus-containing catalysts, comprise phosphorus, e.g. copper phosphides, copper bronzes or alloys of copper with silver and/or gold, copper ores such as malachite and copper or silver compounds which can be reduced completely or partially to copper or silver during the reaction, e.g. copper(I) oxide, silver(I) oxide, copper(II) oxide, and compounds which are converted into copper oxides on heating, e.g. copper nitrate and copper acetate. Other suitable compounds are copper phosphate and copper antimonate. It is also possible for further metal oxides or nonmetal oxides, e.g. the oxides of zinc, chromium, antimony, tin or bismuth, to be mixed into the copper-containing compounds.

The essentially phosphorus-free copper- and/or silver-containing catalysts employed in the present invention have a phosphorus content of from 0 to 400 ppm, preferably from 150 to 400 ppm, corresponding to from 0.015 to 0.04% by weight, and particularly preferably from 150 to 250 ppm, corresponding to from 0.015 to 0.025% by weight, and are preferably in the form of alloys.

An example of an essentially phosphorus-free copper- and/or silver-containing catalyst which is particularly preferred for use in the process of the present invention is copper having the material number 2.0090, which is designated as SF—Cu in accordance with DIN 1708 (cathodes and refinery shapes) and is sold, for example, by Norddeutsche Affinerie AG, Hamburg.

In the process of the present invention, the phosphorus-containing copper- and/or silver-containing catalyst used is a catalyst having a phosphorus content of from >400 to 50,000 ppm, corresponding to from >0.04 to 5% by weight, preferably from >400 to 10,000 ppm, corresponding to from 0.04 to 1% by weight, more preferably from >400 to 1000 ppm, corresponding to from >0.04 to 0.1% by weight, and in particular from 550 to 1000 ppm, corresponding to from 0.055 to 0.1% by weight, in each case based on the catalyst. As phosphorus-containing copper- and/or silver-containing catalyst, preference is given to using a copper-phosphorus alloy having a phosphorus content of from more than 400 to 10,000 ppm which can be produced, for example, by melting copper cathodes grade 1 ASTM B 170 and the copper-phosphorus alloy designated as V-CuP10 in accordance with DIN 17 657 in appropriate ratios. The phosphorus-containing catalyst can be obtained, for example, from Wieland Werke AG, Ulm.

Both the essentially phosphorus-free and the phosphorus-containing copper- and/or silver-containing catalytic composition can also be applied to an inert support or, if desired, diluted with an inert material. The catalyst can, if desired, also be subjected to a reducing treatment before use.

Preference is given to catalysts which do not have a large internal surface area, for example those having a surface area of less than 50 m$^2$ per g. Catalysts which are of particular industrial interest are both essentially phosphorus-free and phosphorus-containing metallic copper or silver and also alloys which comprise copper or silver as a significant constituent.

They are employed, for example, in the form of turnings, woven wire meshes, gauzes or as supported catalysts comprising a, for example, low surface area, inert support. The present invention also provides the catalyst bed itself which is used according to the present invention, i.e. a catalyst bed comprising an essentially phosphorus-free and at least one phosphorus-containing copper- and/or silver-containing catalyst, and also a phosphorus-containing and/or silver-containing catalyst which has a phosphorus content of from 550 to 1000 ppm, based on the catalyst.

The catalyst system used in one embodiment of the process of the present invention which comprises a catalyst bed comprising the essentially phosphorus-free and at least one phosphorus-containing copper- and/or silver-containing catalyst can contain the essentially phosphorus-free and the phosphorus-containing catalyst in various three-dimensional arrangements, i.e. the bed can have various structures.

Thus, the total catalyst bed can consist of a homogeneous mixture of the essentially phosphorus-free and the phosphorus-containing copper- and/or silver-containing catalyst in a weight ratio of from 100:1 to 1:100, preferably from 20:1 to 1:10, particularly preferably from 10:1 to 1:1.

However, it is also possible to use the essentially phosphorus-free copper- and/or silver-containing catalyst for the upper 0.1–50% of the total height of the catalyst bed, preferably the upper 0.1, 10 or 20%, particularly preferably the upper 30–35%, of the total height after the head of the reactor and to make up the remaining catalyst bed of a homogeneous mixture of the essentially phosphorus-free and the phosphorus-containing copper- and/or silver-containing catalyst in a weight ratio of from 100:1 to 1:100, preferably from 20:1 to 1:10, particularly preferably from 10:1 to 1:1. In this preferred structuring of the catalyst bed, the part of the bed which is downstream of the hot spot consists of the homogeneous mixture of essentially phosphorus-free and phosphorus-containing copper- and/or silver-containing catalysts.

Furthermore, the catalyst bed in the region of the upper 0.1–50% of the total height of the catalyst bed, particularly preferably in the region of the upper 1–35% of the catalyst bed, after the head of the reactor can consist of the essentially phosphorus-free copper- and/or silver-containing catalyst while the phosphorus-containing catalyst makes up the remainder of the catalyst bed. In this embodiment of the catalyst bed, the region of the bed downstream of the hot spot consists of the phosphorus-containing catalyst.

For the purposes of the present invention, the hot spot is the part of the catalyst bed at which the highest temperature within the temperature profile of the catalyst bed occurs. The temperature profile of the catalyst bed or the position of the hot spot is usually determined by measuring the temperature within the catalyst bed as a function of the bed height. This can be achieved, for example, by introducing a thermocouple sheath containing a moveable thermocouple or else by means of a fixed multiple thermocouple having a plurality of measurement points at various heights within the bed.

The use of the above-described structured catalyst bed consisting of essentially phosphorus-free and phosphorus-containing copper- and/or silver-containing catalysts has the advantage that the metering-in of phosphorus is technically simple to implement even for large plants.

In a further embodiment of the process of the present invention, a phosphorus compound which is volatile under the reaction conditions can be introduced at the head of the reactor upstream of the catalyst bed or into the catalyst bed in such an amount that the amount of phosphorus (calculated as P) is up to 20 ppm, preferably 0.05 to 20 ppm, based on the weight of alcohol used.

The volatile phosphorus compound can be introduced into any of the above-described, different or differently structured structured catalyst systems or beds.

As far as phosphorus compounds which are volatile under the reaction conditions are concerned, use is advantageously made of phosphorus compounds which can be vaporized without decomposition and undergo no reaction with the components of the synthesis gas under the reaction conditions. These are, for example, esters of phosphoric acid, of phosphorous acid or of phosphonic acid, e.g. trimethyl phosphate, triethyl phosphate, triisopropyl phosphate, tri-n-propyl phosphate, trimethyl phosphite, triethyl phosphite, triethylphosphine oxide, diethyl methylphosphonate, dimethyl methylphosphonate or diethyl ethylphosphonate.

In this embodiment of the process of the present invention, the phosphorus is introduced at the head of the reactor upstream of the catalyst system or within the catalyst system, preferably in the region of the upper 0.1–50% of the total height of the catalyst system, particularly preferably in the region of the upper 1–35% of the catalyst system, after the head of the reactor. Introduction within the catalyst system is preferably carried out downstream of the hot spot. In particular, the phosphorus compound which is volatile under the reaction conditions can be added when using the catalyst bed as catalyst system, in which case the above statements relating to the location or region of the addition of this phosphorus compound are then based on the total height of the catalyst bed.

The phosphorus can be introduced in one or more, preferably two, three or four, parts; the introduction is preferably carried out in two parts of from 0.05 to 10 ppm each, particularly preferably from 0.1 to 3 ppm each.

It is also possible for the phosphorus to be introduced in at least two parts, where (a) the first part is introduced with the gaseous starting mixture upstream of the catalyst system or catalyst bed and (b) at least one further part is introduced within the catalyst system or catalyst bed, preferably in the region of the upper 0.1 to 50%, particularly preferably in the region of the upper 1 to 35%, of the total height of the catalyst system or catalyst bed.

This embodiment of the process of the present invention is, for example, configured such that a gaseous mixture of the alcohol and water in which the water content is from 0.1 to 99% by weight is passed together with air or oxygen in an amount of from 0.5 to 2.0 mol, based on 1 mol of alcohol used, possibly together with nitrogen in an amount of up to 99% by volume of the total gas mixture, over the catalyst held at from 225 to 500° C., with, if desired, the first part of volatile phosphorus compound being added to the gaseous starting mixture and at least one further part being introduced into the catalyst system downstream of the hot spot in the region of 1–35% of the total height of the bed or, if desired, the first part of volatile phosphorus compound being added to the gaseous starting mixture and at least one further part being introduced into the catalyst system downstream of the hot spot in the region of 1–35% of the total height of the system.

Accordingly, the present invention also provides for a method of improving the selectivity and the conversion in oxidation reactions, e.g. oxidative dehydrogenation of alcohols to form carbonyl compounds by adding a volatile phosphorus compound as defined above which is is volatile under the reaction conditions or of a phosphorus-containing copper- and/or silver-containing catalyst or of a combination of the phosphorus compound and the catalyst into the reactor for and for lowering the COX selectivity in the preparation of carbonyl compounds starting from alcohols and/or for controlling the temperature of the hot spot in the preparation of carbonyl compounds starting from alcohols by adding such a phosphorus compound or such a catalyst or such a combination into the reactor.

The gas mixture leaving the reactor is usually scrubbed with water.

The phosphorus compound can be introduced as a solution in water, alcohol, preferably the alcohol used, or suitable solvents, for example ethers, in liquid or, by vaporization of the solution, in gaseous form or else in the form of a pure gaseous phosphorus compound, preference being given to introduction as vaporized solution or in pure gaseous form.

The glyoxal obtained from ethylene glycol according to the process of the present invention which can be obtained directly in the commercial form of a 40% strength by weight aqueous solution, has a high purity which remains untouched even for a long operating time. The process of the present invention gives glyoxal in high yields with long catalyst operating lives.

The process of the present invention is illustrated by the following examples.

EXAMPLE 1

In a titanium tube reactor having an internal diameter of 20 mm, shaped catalyst bodies of essentially phosphorus-free copper catalyst made of SF—Cu (DIN 1708 material number 2.0090) and shaped catalyst bodies of a copper-phosphorus alloy having a phosphorus content of 1000 ppm were installed with a catalyst height of 300 mm (catalyst volume 95 ml) and with such a structure that the upper 10 cm of the catalyst bed after the head of the reactor consisted of the essentially phosphorus-free catalyst and the remainder of the bed (from 10 to 30 cm after the head of the reactor) consisted of the phosphorus-containing copper-phosphorus alloy. A synthesis mixture consisting of 130 l/h (s.t.p.) of nitrogen and air and 12.4 g/h of ethylene glycol was passed through the tube reactor. The reactor temperature was set to 360° C. by means of a salt melt.

The GHSV (gas hourly space velocity), which is defined as

GHSV=gas volume/catalyst volume,
was 1500 $h^{-1}$. The LHSV (liquid hourly space velocity), which is defined as LHSV=liquid volume/catalyst volume,
was 0.12 $h^{-1}$. The residence time defined as the ratio of the catalyst volume and the amount of gas was 2.4 s.

After leaving the reactor, the reaction gas was brought into contact with water, with the reaction products being dissolved in the aqueous phase. The permanent gases CO and $CO_2$ formed in the reaction and unreacted $O_2$ remained in the tailgas and were analyzed in the gas phase.

The experimental result obtained after a running time of 10 days at different conversions is summarized in Table 1 below.

EXAMPLE 2

The catalyst bed in the tube reactor described in Example 1 was structured such that the upper 10 cm after the head of the reactor consisted of shaped bodies of the essentially phosphorus-free copper catalyst SF—Cu and the remainder of the bed (from 10 to 30 cm after the head of the reactor) consisted of a 1:10 mixture (on a weight basis) of shaped bodies of a copper-phosphorus alloy having a phosphorus content of 10,000 ppm and shaped bodies of the essentially phosphorus-free catalyst SF—Cu.

Using a method similar to Example 1, 12.4 g/h of ethylene glycol and 130 l/h (s.t.p.) of a mixture of nitrogen and air were passed through the tube reactor.

The experimental result obtained after a running time of 10 days at various conversions is summarized in Table 1 below.

EXAMPLE 3

The tube reactor described in Example 1 was charged over its total fill height of 300 mm with a 1:5 mixture (on a weight basis) of shaped catalyst bodies of a copper-phosphorus alloy having a phosphorus content of 10,000 ppm and shaped bodies of the essentially phosphorus-free copper catalyst SF—Cu.

Using a method similar to Example 1, 12.4 g/h of ethylene glycol and 130 l/h (s.t.p.) of a mixture of nitrogen and air were passed through the tube reactor.

The experimental result obtained after a running time of 10 days at various conversions is summarized in Table 1 below.

EXAMPLE 4

The tube reactor described in Example 1 was charged over its total fill height of 300 mm with a 1:10 mixture (on a weight basis) of shaped bodies of a copper-phosphorus alloy having a phosphorus content of 10,000 ppm and shaped bodies of the essentially phosphorus-free copper catalyst SF—Cu.

Using a method similar to Example 1, 12.4 g/h of ethylene glycol and 130 l/h (s.t.p.) of a mixture of nitrogen and air were passed through the reactor.

The experimental result obtained after a running time of 10 days at various conversions is summarized in Table 1 below.

COMPARATIVE EXAMPLE C1

The tube reactor described in Example 1 was charged over its total bed height with the essentially phosphorus-free, shaped catalyst bodies made of SF—Cu.

Using a method similar to Example 1, 12.4 g/h of ethylene glycol and 130 l/h (s.t.p.) of a mixture of nitrogen and air were passed through the reactor.

The experimental result obtained after a running time of 10 days at various conversions is summarized in Table 1 below.

COMPARATIVE EXAMPLE C2

The tube reactor described in Example 1 was charged over its total bed height with shaped catalyst bodies of a copper-phosphorus alloy having a phosphorus content of 10,000 ppm.

Using a method similar to Example 1, 12.4 g/h of ethylene glycol and 130 l/h (s.t.p.) of a mixture of nitrogen and air were passed through the tube reactor.

The experimental result obtained after a running time of 10 days at various conversions is summarized in Table 1 below.

TABLE 1

| Example | Ethylene glycol conversion [Mol %] | Glyoxal Selectivity [%] | $CO/CO_2$ Selectivity [%] | Air [l/h (s.t.p.)] |
|---|---|---|---|---|
| 1 | 95.6 | 79.5 | 16.0 | 38 |
| 1 | 97.4 | 75.6 | 18.5 | 40 |
| 1 | 98.2 | 73.1 | 19.6 | 40 |
| 1 | 99.5 | 67.4 | 24.5 | 42 |
| 2 | 91.5 | 81.4 | 12.3 | 34 |
| 2 | 96.5 | 80.7 | 15.4 | 36 |
| 2 | 98.4 | 79.1 | 21.3 | 38 |
| 2 | 99.0 | 74.5 | 27.8 | 40 |
| 3 | 96.7 | 72.1 | 19.3 | 40 |
| 3 | 97.4 | 68.9 | 21.5 | 41 |
| 3 | 97.8 | 67.3 | 23.5 | 42 |
| 4 | 96.4 | 71.0 | 19.5 | 34 |
| 4 | 97.9 | 68.1 | 23.1 | 35 |
| C1 | 95.3 | 70.5 | 19.4 | 37 |
| C1 | 96.7 | 69.3 | 20.5 | 36 |
| C1 | 98.8 | 60.0 | 36.3 | 38 |
| C1 | 99.6 | 54.9 | 41 | 40 |
| C2 | 95.2 | 58.1 | 25.2 | 22 |
| C2 | 96.9 | 55.7 | 27.3 | 24 |
| C2 | 98.2 | 51.4 | 31.4 | 26 |
| C2 | 99.5 | 49.7 | 34.4 | 28 |

EXAMPLE 5

In a stainless steel tube reactor having an internal diameter of 54 mm, shaped catalyst bodies of essentially phosphorus-free copper catalyst SF—Cu (DIN 1708 material number 2.0090) and shaped catalyst bodies of a copper-phosphorus alloy having a phosphorus content of 10,000 ppm were installed such that, of the 250 cm catalyst fill height (catalyst volume 5.7 l), the first 59 cm after the head of the reactor consisted of essentially phosphorus-free copper catalyst and the remainder of the bed (from 60 to 250 cm) consisted of a homogeneous 1:10 mixture (on a weight basis) of shaped bodies of the copper-phosphorus alloy having a phosphorus content of 10,000 ppm and shaped bodies of the essentially phosphorus-free copper catalyst SF—Cu.

A synthesis gas mixture consisting of 870 g/h of ethylene glycol, 1880 l/h (s.t.p.) of air and 80 l/h (s.t.p.) of nitrogen was passed through the tube reactor. The reactor temperature was set to 365° C. by means of a salt melt.

The total amount of gas, consisting of circulating gas and synthesis gas, was 9500 l/h (s.t.p.). The GHSV (gas hourly space velocity) was 1650 h$^{-1}$. The LHSV (liquid hourly space velocity) was 0.13 h$^{-1}$. The residence time was 2.2 s.

After leaving the reactor, the reaction gas was brought into contact with water, with the reaction products being dissolved in the aqueous phase. The permanent gases CO and CO$_2$ formed in the reaction and unreacted O$_2$ remained in the tailgas and were analyzed in the gas phase.

The experimental result obtained after a running time of 10 days is summarized in Table 2.

EXAMPLE 6

In a stainless steel tube reactor having an internal diameter of 54 mm, shaped catalyst bodies of essentially phosphorus-free copper catalyst SF—Cu (DIN 1708 material number 2.0090) and shaped catalyst bodies of a copper-phosphorus alloy having a phosphorus content of 1000 ppm were installed such that, of the 250 cm catalyst fill height (catalyst volume 5.7 l), the first 16 cm after the head of the reactor consisted of the essentially phosphorus-free copper catalyst and the remainder of the bed (from 17 to 250 cm) consisted of shaped bodies of the phosphorus-containing copper-phosphorus alloy having a phosphorus content of 1000 ppm.

A synthesis gas mixture consisting of 870 g/h of ethylene glycol, 1760 l/h (s.t.p.) of air and 80 l/h (s.t.p.) of nitrogen was passed through the tube reactor. The reactor temperature was set to 365° C. by means of a salt melt.

The total amount of gas, consisting of circulating gas and synthesis gas, was 9500 l/h (s.t.p.). The GHSV (gas hourly space velocity) was 1650 h$^{-1}$. The LHSV (liquid hourly space velocity) was 0.13 h$^{-1}$. The residence time was 2.2 s.

After leaving the reactor, the reaction gas was brought into contact with water, with the reaction products being dissolved in the aqueous phase. The permanent gases CO and CO$_2$ formed in the reaction and unreacted O$_2$ remained in the tailgas and were analyzed in the gas phase.

The experimental result obtained after a running time of 10 days is summarized in Table 2.

EXAMPLE 7

In the tube reactor described in Example 6, 7.8 kg of a Cu catalyst doped with 600 ppm and having the form of rings were installed in place of the catalyst bed described in Example 6. The catalyst fill height was likewise 250 cm (catalyst volume 5.7 l).

Subsequently, the reaction to form glyoxal from ethylene glycol was carried out using a method similar to Example 6 but using 1700 standard l of air in place of 1760 standard l of air and 140 standard l of nitrogen in place of 80 standard l of nitrogen in the synthesis gas mixture.

The work-up was carried out by a method similar to Example 5.

The experimental result obtained after a running time of 10 days is shown in Table 2.

COMPARATIVE EXAMPLE C3

The procedure of Example 5 was repeated. However, the catalyst bed consisted over its total height of shaped bodies of the essentially phosphorus-free copper catalyst SF—Cu. Product work-up was carried out as described in Example 5. The experimental result obtained after a running time of 10 days is summarized in Table 2.

COMPARATIVE EXAMPLE C3

The procedure of Example C3 was repeated. 0.3 ppm of phosphorus (P), based on the weight of ethylene glycol used, in the form of triethyl phosphate was added to the synthesis gas mixture at the head of the reactor upstream of the catalyst bed.

Product work-up was carried out as described in Example 5. The experimental result obtained after a running time of 10 days is summarized in Table 2.

A comparison of the results achieved in Example 2 according to the present invention with those obtained in Comparative Examples C3 and C4 which are not according to the present invention is shown in Table 2 below.

In all of the above Examples 5 to 7 and C3 and C4, the air was chosen so as to enable the selectivities at different conversions to be compared.

TABLE 2

| Example | Ethylene glycol conversion [Mol %] | Glyoxal Selectivity [%] | CO/CO$_2$ Selectivity [%] | Glycol aldehyde Selectivity [mol %] | Formaldehyde Selectivity [mol %] | Air [l (s.t.p.)/h] |
|---|---|---|---|---|---|---|
| 5 | 98.2 | 80.9 | 14.0 | 1.73 | 2.2 | 1880 |
| 6 | 98.3 | 82.5 | 10.3 | 0.65 | 3.8 | 1760 |
| 7 | 98.1 | 85.3 | 7.4 | 0.94 | 2.73 | 1700 |
| C3 | 98.2 | 75.1 | 15.2 | 0.8 | 5.9 | 1800 |
| C4 | 98.8 | 76.9 | 14.0 | 1.1 | 5.9 | 1720 |

We claim:
1. A process for preparing carbonyl compounds of the formula

(I)

where R$^1$ is a hydrogen atom or an alkyl radical having from 1 to 3 carbon atoms, R$^2$ is a hydrogen atom, an unsubstituted or C$_1$–C$_3$-alkyl-monosubstituted to -trisubstituted C$_2$–C$_4$-alkenyl radical or a radical of the formula

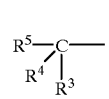

(II)

where R$^3$ is a hydrogen atom or together with R$^4$ is an oxygen atom, R$^4$ is the radical OR$^6$ or together with R$^3$ is an oxygen atom, R$^5$ is a hydrogen atom, an alkyl radical having from 1 to 8 carbon atoms, and unsubstituted or C$_1$–C$_3$-alkyl-monosubstituted to -trisubstituted C$_2$–C$_4$-alkenyl radical or a cyclohexyl or cyclopentyl radical and R$^6$ is an alkyl radical having from 1 to 4 carbon atoms, a cyclohexyl or cyclopentyl radical or a radical of the formula —CH$_2$—CHO or —CH$_2$—CH$_2$—O—CH$_2$—CHO, by gas-phase oxidation of methanol or alcohols of the formula

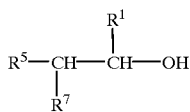
(III)

where $R^1$ and $R^5$ are as defined above, and $R^7$ is a hydrogen atom or a radical $OR^8$ wherein $R^8$ is a hydrogen atom, an alkyl radical having from 1 to 4 carbon atoms, a cyclohexyl or cyclopentyl radical or a radical of the formula $CH_2$—$CH_2$—OH or —$CH_2$—$CH_2$—O—$CH_2$—OH, by means of an oxygen-containing gas in the presence of copper- and/or silver-containing catalysts, wherein the catalyst system used comprises at least one phosphorus-containing (>400 to 50,000 ppm phosphorus) copper- and/or silver-containing catalyst, which is not volatile under the reaction conditions and which is selected from the group consisting of a copper-phosphorus alloy, a silver-phosphorus alloy, copper phosphide, copper phosphate, phosphorus-containing metallic copper, or phosphorus-containing metallic silver.

2. A process as claimed in claim 1, wherein said at least one phosphorus-containing copper- and/or silver-containing catalyst has a phosphorus content of from >400 to 110,000 ppm (>0.04 to 1% by weight), based on the catalyst.

3. A process as claimed in claim 1, wherein said at least one phosphorus-containing copper- and/or silver-containing catalyst has a phosphorus content of from 550 to 1000 ppm (0.055 to 0.1% by weight), based on the catalyst.

4. A process as claimed in claim 1, wherein said catalyst system comprises a catalyst bed comprising both an essentially phosphorus-free (0 to 400 ppm phosphorus) copper- and/or silver-containing catalyst and said at least one phosphorus-containing copper- and silver-containing catalyst.

5. A process as claimed in claim 4, wherein the catalyst bed comprises a mixture of said essentially phosphorus-free catalyst and said phosphorus-containing catalyst in a ratio of from 100:1 to 1:100.

6. A process as claimed in claim 5, wherein the upper 0.1–50% of the total height of the catalyst bed after the head of the reactor consists only of said essentially phosphorus-free catalyst and the remainder of the catalyst bed consists of said mixture.

7. A process as claimed in claim 4, wherein the catalyst bed in the region of the upper 0.1–50% of the total height of the catalyst bed consists of said essentially phosphorus-free catalyst and the remainder of the catalyst bed consists of said phosphorus-containing catalyst.

8. A process as claimed in claim 1, wherein a phosphorus compound which is volatile under the reaction conditions is introduced at the head of the reactor or into the catalyst bed in the region of the upper 0.1–50% of the total height of the catalyst system or both.

9. A process as claimed in claim 8, wherein the amount of phosphorus (calculated as P) introduced in the form of the volatile phosphorus compound is from 0.05 to 20 ppm, based on the weight of the alcohol used.

10. A process as claimed in claim 8, wherein the phosphorus introduced in the form of the volatile phosphorus compound is introduced in at least two parts, where (a) the first part is introduced with the gaseous starting mixture upstream of the catalyst system and (b) at least one further part is introduced within the catalyst system.

11. A process as claimed in claim 10, wherein said at least one further part b) is introduced into the catalyst system in the region of the upper 0.1–50% of the total height of the catalyst system.

12. A process as claimed in claim 1, wherein glyoxal is prepared from ethylene glycol or methylglyoxal is prepared from propylene glycol.

13. The process as claimed in claim 1, wherein said phosphorus containing catalyst is a copper-phosphorus alloy, a silver-phosphorus alloy or copper phosphide.

14. The process as claimed in claim 1, wherein said essentially phosphorus-free catalyst is a compound which can be converted to copper oxide, silver oxide or metallic copper or silver on heating.

* * * * *